United States Patent [19]
Nitoh et al.

[11] Patent Number: 5,149,871
[45] Date of Patent: Sep. 22, 1992

[54] WATER-SOLUBLE THIOUREA DIOXIDE DERIVATIVES AND PROCESS FOR PREPARING SAME

[75] Inventors: Hirohisa Nitoh; Osami Ohura, both of Fuji; Morio Suzuki, Hamamatsu, all of Japan

[73] Assignee: Tokai Denka Kogyo Kabushiki Kaisha, Tokyo, Japan

[21] Appl. No.: 797,789

[22] Filed: Nov. 25, 1991

[30] Foreign Application Priority Data

Nov. 29, 1990 [JP] Japan ................................. 2-325432

[51] Int. Cl.$^5$ ............................................. C07C 315/00
[52] U.S. Cl. .................................................... 562/556
[58] Field of Search ......................................... 562/556

[56] References Cited

U.S. PATENT DOCUMENTS 3,121,111 2/1964 Berger ............................... 562/556

Primary Examiner—Michael L. Shippen
Attorney, Agent, or Firm—Scully, Scott, Murphy & Presser

[57] ABSTRACT

A novel water-soluble produced by contacting thiourea dioxide with an aqueous solution comprising an amino acid having the general formula $NH_2(CH_2)_n COOH$ wherein n is an integer of 1 to 7 and a sodium, potassium or calcium salt of acetic acid.

5 Claims, 6 Drawing Sheets

WATER-SOLUBLE THIOUREA DIOXIDE DERIVATIVES AND PROCESS FOR PREPARING SAME

BACKGROUND OF THE INVENTION

The present invention relates to novel water-soluble thiourea dioxide derivatives and a process for preparing same.

Thiourea dioxide is in wide use as a reducing agent in the dying industry and the photographic industry because it exhibits a strong reducing ability in a basic aqueous solution.

In the polymer industry and the field of organic chemistry, moreover, studies have been made about using thiourea dioxide as a stabilizer for various compounds (see U.S. Pat. Nos. 2,472,868 and 3,070,569), as a curing agent for amino resins (see German Patent No. 1,215,363 and French Patent No. 1,445,045), or as a polymerization initiator in the polymerization of vinyl monomers using thiourea dioxide together with iron-hydrogen peroxide (see Am. Dyest. Dep. 75, 26–34 (1986). And actually thiourea dioxide has come to be used as such agents gradually.

In the field of polymer industry and that of organic chemical industry, however, the application range thereof is limited because thiourea dioxide is insoluble in almost all organic solvents, and its industrial use in these fields is actually very limited. Although thiourea dioxide dissolves in water, the solubility thereof is 30 g/l or so, which is not always sufficient, depending on the field in which it is used.

Several derivatives of thiourea dioxide have also been proposed with a view to improving the solubility and other properties and expanding the application field. For example, in J. Chem. Soc. Perkin II. 4.1500 (1972) and Synth. Commun. 4.389 (1974) there is proposed a method wherein thiourea derivatives such as N,N'-diphenylthiourea, N,N'-dibenzylthiourea and N,N'-dicyclohexylthiourea are oxidized with hydrogen peroxide to prepare corresponding thiourea dioxide derivatives. However, this method is of little industrial utility because it is difficult to obtain such starting thioureas industrially.

It is the object of the present invention to provide novel thiourea dioxide derivatives superior in water-solubility as compared with thiourea dioxide, having a sufficient reducing ability and capable of being manufactured easily from materials which are easily available industrially.

SUMMARY OF THE INVENTION

The novel thiourea dioxide derivatives of the present invention are represented by the following general formula:

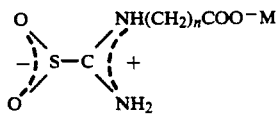

wherein M is $K^+$, $Na^+$, or $\frac{1}{2} Ca^{2+}$, and n is an integer of 1 to 7.

The thiourea dioxide derivatives of the above general formula (I) can each be prepared efficiently be adding thiourea dioxide into an aqueous solution comprising an amino acid represented by the following formula and a sodium, potassium or calcium salt of acetic acid and allowing reaction to take place under temperature and time conditions sufficient for the formation of the derivative:

wherein n is an integer of 1 to 7.

DETAILED DESCRIPTION OF THE INVENTION

The above manufacturing process is represented as follows in terms of a reaction formula in the case of using glycine as the amino acid and sodium acetate as the acetic acid salt:

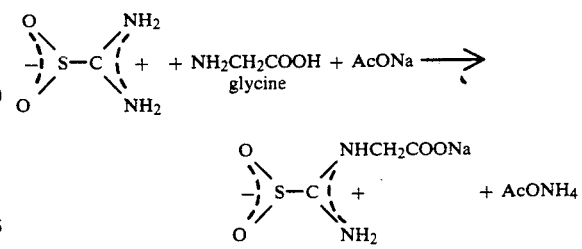

The amino acid used in the above manufacturing process may essentially be any amino acid if only it is represented by the general formula (II). But unbranched straight-chain amino acids are preferred. Examples are glycine, β-alanin, 4-amino-n-butyric acid, 5-aminovaleric acid, 6-amino-n-caproic acid, and 8-amino-n-caprylic acid. As the acetic acid salt there is used sodium salt, potassium salt or calcium salt of acetic acid.

The amounts of thiourea dioxide, amino acid and acetic acid salt to be used are determined on the basis of a conventional stoichiometric reaction and in accordance with the foregoing reaction formula.

The reaction temperature is usually in the range of 10° to 80° C., preferably 25° to 40° C.

It is preferable that the reaction be carried out usually in an aqueous system after purging the interior of the system with an inert gas such as nitrogen gas. But the reaction may be performed even in the air.

The thiourea dioxide derivatives of the general formula (I) thus obtained have an excellent reducing ability and exhibit an extremely superior water solubility. For example, the water solubility of the sodium-substituted derivative of glycine shown by the foregoing reaction formula is 300 g/l and that of a potassium-substituted derivative thereof is 500 g/l. The following examples are given to further illustrate the present invention, but it is to be understood that the invention is not limited thereto.

EXAMPLE-1

Glycine Sodium Salt-Substituted Derivative 41.3 g (0.55 mol) of glycine and 74.8 g (0.55 mol) of sodium acetate were dissolved in 150 ml of water in a nitrogen gas atmosphere, into which was added 54.0 g (0.5 mol) of thiourea dioxide little by little, and stirring was made at room temperature for 4 hours.

After completion of the reaction, water was distilled off until the total amount was reduced to half. Then, 30 ml of methanol was added to precipitate crystals, followed by washing with cold methanol to yield 82.4 g (80% yield) of white crystals having a maximum absorption at 267 nm, decomp. 141°-145° C.

IR spectrum is as shown in FIG. 1. The crystals were dissolved in water at a rate of 310 g/l.

EXAMPLE-2

β-Alanine Sodium Salt-Substituted Derivative 49.0 g (0.55 mol) of β-alanine, 74.8 g (0.55 mol) of sodium acetate, 54.1 g (0.5 mol) of thiourea dioxide and 150 ml of water were stirred at room temperature for 6 hours as in Example 1.

There were obtained 79.2 g (75% yield) of while crystals having a maximum absorption at 267 nm, decomp. 198°-205° C. IR spectrum is as shown in FIG. 2. The crystals were dissolved in water at a rate of 350 g/l.

EXAMPLE-3

4-Amino-N-Butyric Acid Sodium Salt-Substituted Derivative 56.7 g (0.55 mol) of 4-amino-n-butyric acid, 74.8 g (0.55 mol) of sodium acetate, 54.1 g (0.5 mol) of thiourea dioxide and 100 ml of water were stirred at room temperature for 6 hours as in Example 1.

There were obtained 89.7 g (83% yield) of while crystals having a maximum absorption at 266 nm, decomp. 172°-175° C. IR spectrum is as shown in FIG. 3. The crystals were dissolved in water at a rate of 350 g/L.

6-Amino-N-Caproic Acid Sodium Salt-Substituted Derivative 72.1 g (0.55 mol) of 6-amino-n-caproic acid, 74.8 g (0.55 mol) of sodium acetate, 54.1 g (0.5 mol) of thiourea dioxide and 100 ml of water were stirred at room temperature for 8 hours as in Example 1.

There were obtained 64.7 g (53% yield) of white crystals having a maximum absorption at 272 nm, decomp. 170°-172° C. IR spectrum is as shown in FIG. 4. The crystals were dissolved in water at a rate of 380 g/l.

EXAMPLE-5

Glycine Pottasium Salt-Substituted Derivative 41.3 g (0.55 mol) of glycine, 54.0 g (0.55 mol) of potassium acetate, 54.1 g (0.5 mol) of thiourea dioxide and 100 ml of water were stirred at room temperature for 6 hours as in Example 1.

There were obtained 76.6 g (75% yield) of white crystals having a maximum absorption at 262 nm, decomp. 135°-138° C. IR spectrum is as shown in FIG. 5. The crystals were dissolved in water at a rate of 490 g/l.

EXAMPLE-6

Glycine-Calcium Salt-Substituted Derivative 0 41.3 g (0.55 mol) of glycine, 48.4 g (0.28 mol) of calcium acetate, 54.1 g (0.5 mol) of thiourea dioxide and 150 ml of water were stirred at room temperature for 3 hours as in Example 1.

There were obtained 94.5 g (89% yield) of white crystals having a maximum absorption at 268 nm, decomp. 173°-175° C. IR spectrum is as shown in FIG. 6.

Figure 1:
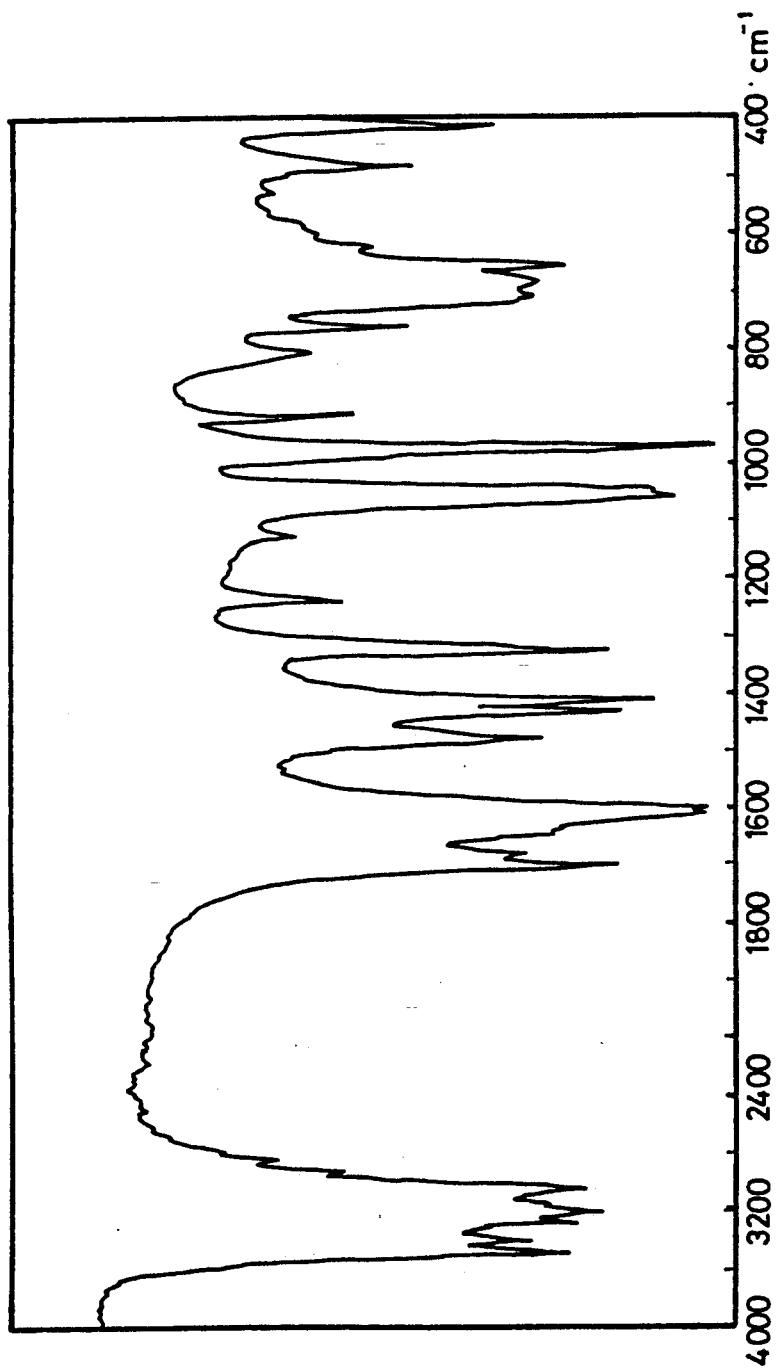
FIGS. 1 to 6 show IR spectra of the thiourea dioxide derivatives prepared in the working Examples.
Figure 2:
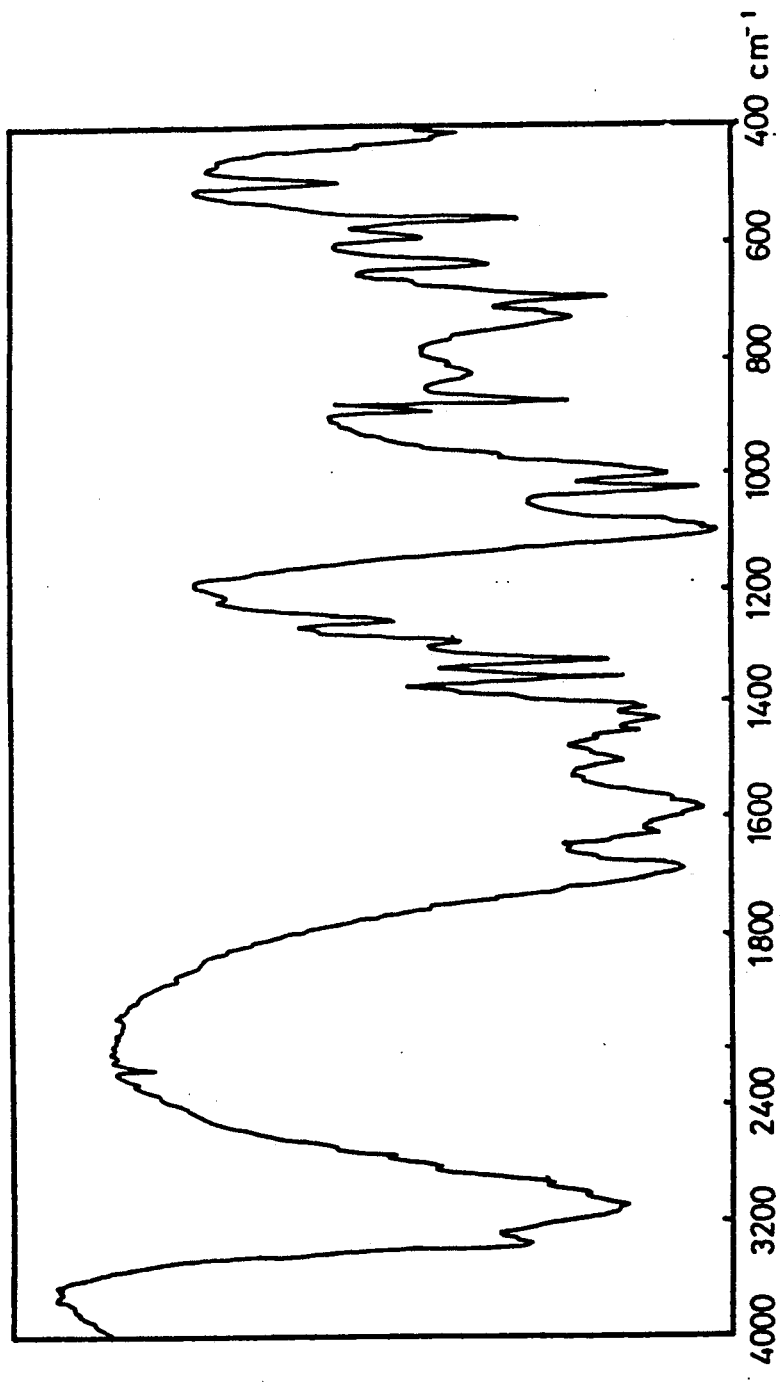
Figure 3:
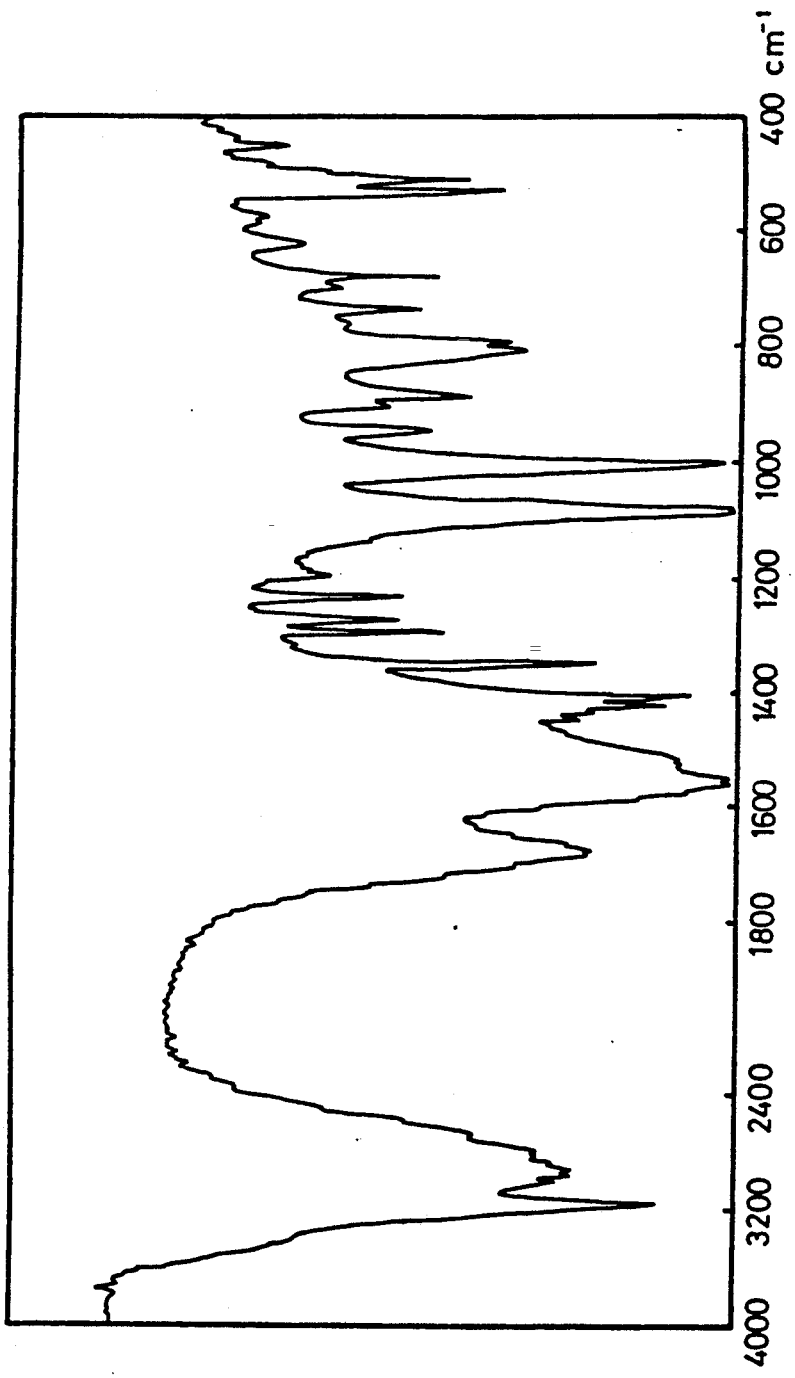
Figure 4:
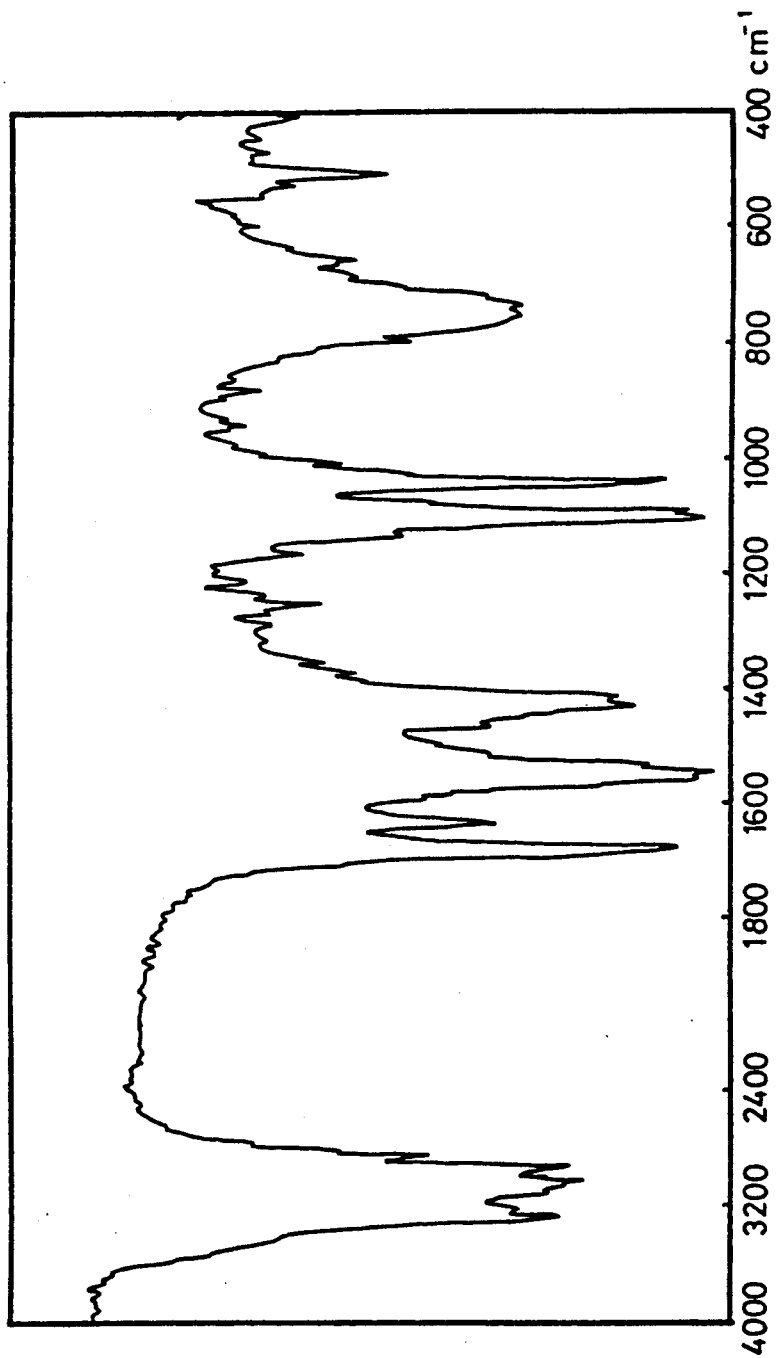
Figure 5:
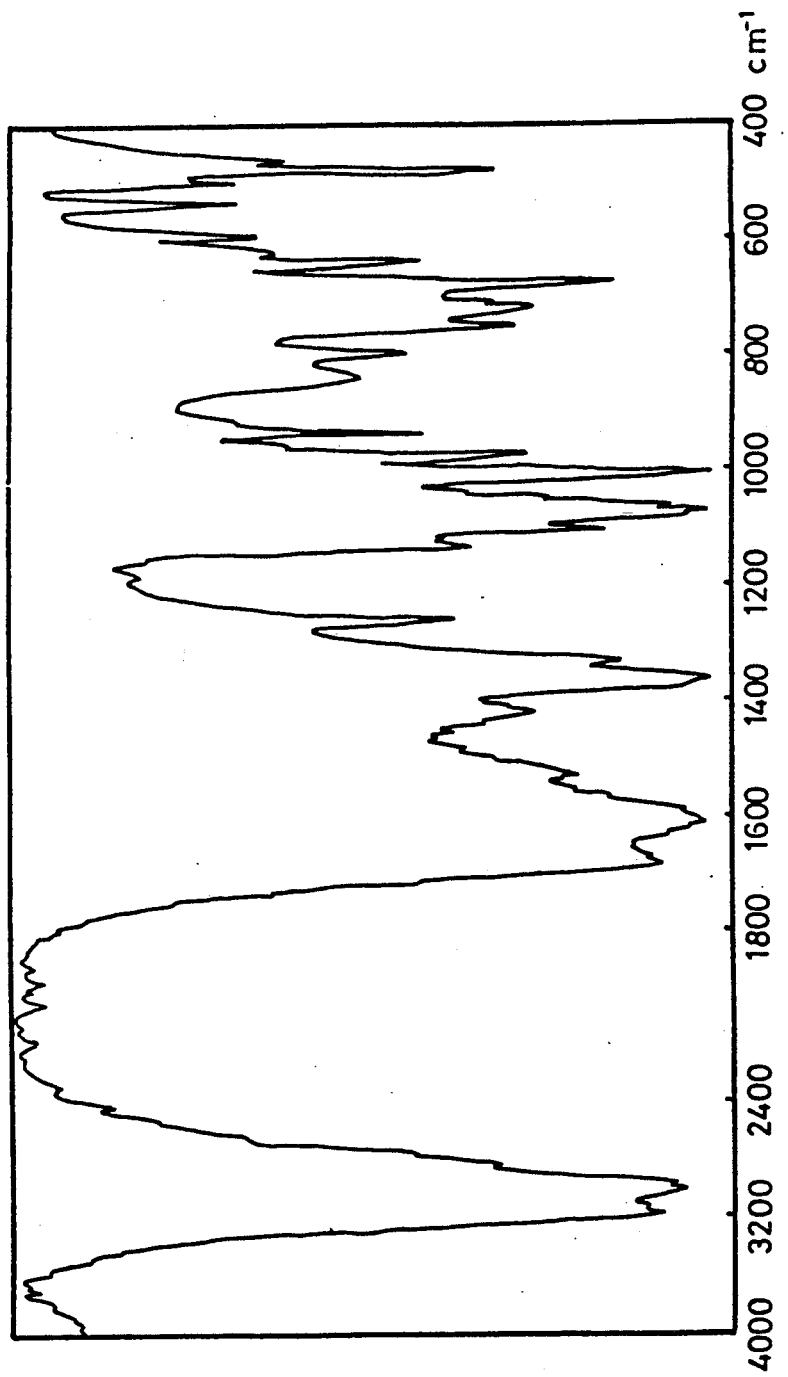
Figure 6:
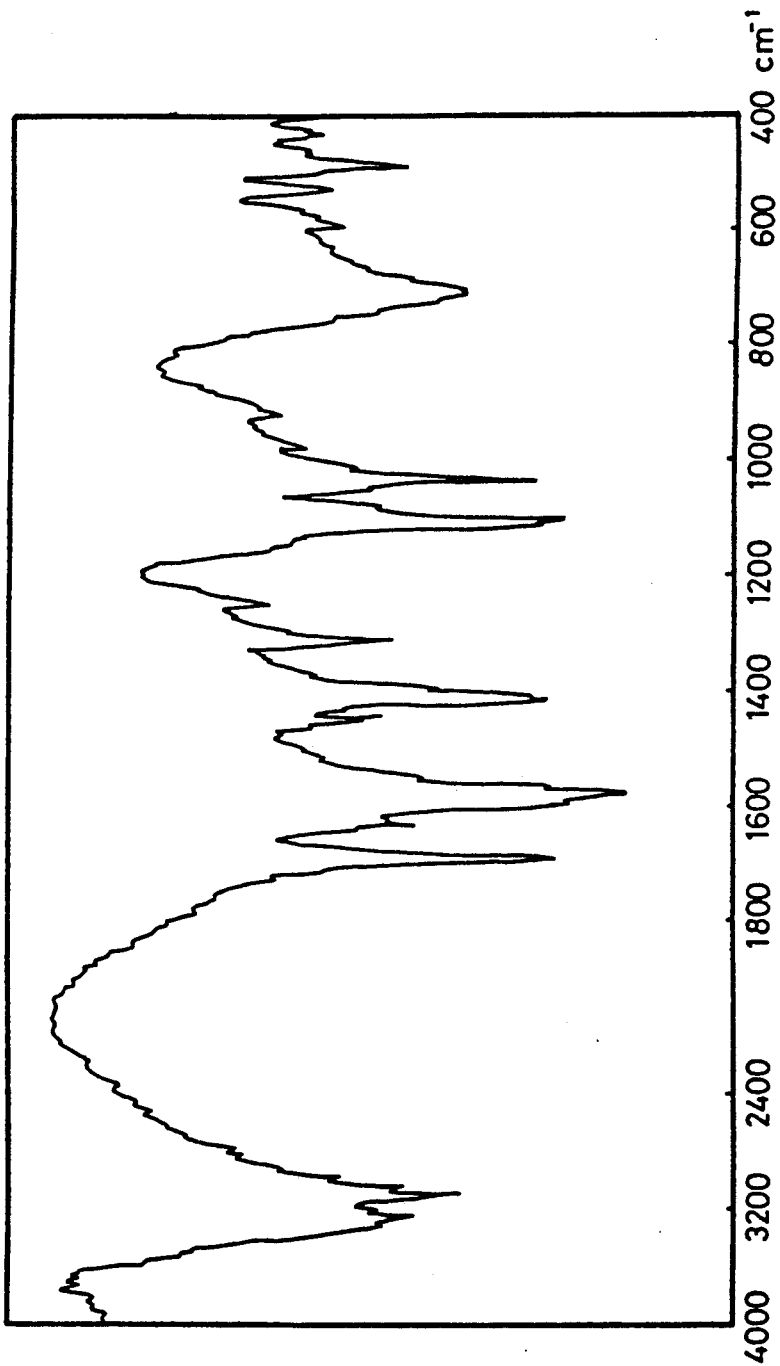

What is claimed is:

1. A water-soluble thiourea dioxide derivative represented by the general formula

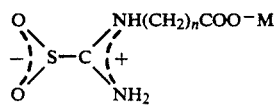

wherein M is $K^+$, $Na^+$, or $\frac{1}{2} CA^{2+}$, and n is an integer of 1 to 7.

2. A process for preparing a water-soluble thiourea dioxide derivative represented by the general formula

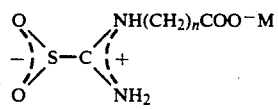

wherein M is $K^+$, $Na^+$, or $\frac{1}{2} Ca^{2+}$, and n is an integer of 1 to 7, which comprises adding thiourea dioxide into an aqueous solution comprising an amino acid represented by the following general formula and a sodium, potassium or calcium salt of acetic acid:

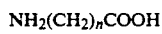

wherein n is an integer of 1 to 7 and allowing reaction to take place under temperature and time conditions sufficient to produce the thiourea derivative.

3. A process as set forth in claim 2, wherein the amino acid is glycine, β-alanine, 4-amino-n-butyric acid, 5-amino-valeric acid, 6-amino-n-caproic acid, or 8-amino-n-caprylic acid.

4. A process as set forth in claim 2, wherein the reaction is performed at a temperature of 10° to 80° C.

5. A process as set forth in claim 2, wherein the thiourea dioxide, amino acid and acetic acid salt are used each in a substantially stoichiometric amount.

* * * * *

UNITED STATES PATENT AND TRADEMARK OFFICE
CERTIFICATE OF CORRECTION

PATENT NO. : 5,149,871
DATED : September 22, 1992
INVENTOR(S) : Hiroshisa Nitoh, et al.

It is certified that error appears in the above-identified patent and that said Letters Patent is hereby corrected as shown below:

Column 3, line 9: "8-alanine" should read as --$\beta$-alanine--

Column 3, line 30: "g/L" should read as --g/$\ell$--

Column 4, line 4: delete first occurrence of "0"

Column 4, line 25, Claim 1: "CA" should read as --Ca--

Column 4, line 47, Claim 3: "8-alanine" should read as --$\beta$-alanine--

Signed and Sealed this

Fifth Day of October, 1993

BRUCE LEHMAN

*Attest:*

*Attesting Officer*  Commissioner of Patents and Trademarks